(12) United States Patent
Maack et al.

(10) Patent No.: US 10,136,864 B2
(45) Date of Patent: Nov. 27, 2018

(54) X-RAY COLLIMATOR SIZE AND POSITION ADJUSTMENT BASED ON PRE-SHOT

(71) Applicants: KONINKLIJKE PHILIPS N.V., Eindhoven (NL); PHILIPS DEUTSCHLAND GMBH, Hamburg (DE)

(72) Inventors: Hanns-Ingo Maack, Norderstedt (DE); Christoph Kurze, Hamburg (DE); Jens Von Berg, Hamburg (DE); André Goossen, Radbruch (DE); Claire Levrier, Rueil-Malmaison (FR); Raoul Florent, Ville D'Avray (FR); Liesbet Hilde Hadewijch Roose, Hamburg (DE); Dirk Manke, Hamburg (DE); Marc Hensel, Bad Oldesloe (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 324 days.

(21) Appl. No.: 14/766,163

(22) PCT Filed: Feb. 14, 2014

(86) PCT No.: PCT/EP2014/052955
§ 371 (c)(1),
(2) Date: Aug. 6, 2015

(87) PCT Pub. No.: WO2014/125090
PCT Pub. Date: Aug. 21, 2014

(65) Prior Publication Data
US 2015/0374314 A1    Dec. 31, 2015

(30) Foreign Application Priority Data

Feb. 15, 2013  (EP) .................................... 13155428

(51) Int. Cl.
*A61B 6/06* (2006.01)
*A61B 6/00* (2006.01)

(52) U.S. Cl.
CPC .............. *A61B 6/06* (2013.01); *A61B 6/4085* (2013.01); *A61B 6/4405* (2013.01);
(Continued)

(58) Field of Classification Search
CPC ......... A61B 6/06; A61B 6/488; A61B 6/4085; A61B 6/4405
(Continued)

(56) References Cited

U.S. PATENT DOCUMENTS

| 3,502,878 A | 3/1970 | Stewart et al. |
|---|---|---|
| 6,055,295 A | 4/2000 | Murthy et al. |

(Continued)

FOREIGN PATENT DOCUMENTS

| JP | 60190934 A | 9/1985 |
|---|---|---|
| JP | 2006122488 A | 5/2006 |

(Continued)

*Primary Examiner* — Courtney Thomas
(74) *Attorney, Agent, or Firm* — Larry Liberchuk

(57) ABSTRACT

An X-ray apparatus for image acquisition and a related method. The apparatus comprises a field-of-view corrector (CS) configured to receive a scout image (SI) acquired by the imager with a tentative collimator setting in a pre-shot imaging phase where said imager operates with a low dosage radiation cone causing the detector to register the scout image. The low dosage cone has, in the detector's image plane, a first cross section smaller than the total area of the detector surface. The field-of-view corrector (CS) uses said scout image to establish field-of-view correction information for a subsequent imaging phase where the imager is to operate with a high dosage radiation cone, the high dosage higher than the low dosage.

20 Claims, 6 Drawing Sheets

(52) U.S. Cl.
CPC ............ *A61B 6/4452* (2013.01); *A61B 6/488* (2013.01); *A61B 6/545* (2013.01); *A61B 6/587* (2013.01); *A61B 6/588* (2013.01)

(58) Field of Classification Search
USPC ........................................................ 378/205
See application file for complete search history.

(56) References Cited

U.S. PATENT DOCUMENTS

| | | | | |
|---|---|---|---|---|
| 6,106,152 | A | * | 8/2000 | Thunberg ................. A61B 6/06 |
| | | | | 348/E5.086 |
| 6,795,526 | B2 | | 9/2004 | Kump et al. |
| 6,827,489 | B2 | | 12/2004 | Nicolas et al. |
| 7,313,224 | B1 | | 12/2007 | Saunders |
| 2003/0165216 | A1 | | 9/2003 | Walker et al. |
| 2011/0013752 | A1 | | 1/2011 | Takahashi |
| 2012/0128125 | A1 | | 5/2012 | Jabri et al. |

FOREIGN PATENT DOCUMENTS

| | | |
|---|---|---|
| WO | 2008023301 A2 | 2/2008 |
| WO | 2013190440 A1 | 12/2013 |

* cited by examiner

X-RAY COLLIMATOR SIZE AND POSITION ADJUSTMENT BASED ON PRE-SHOT

CROSS-REFERENCE TO PRIOR APPLICATIONS

This application is the U.S. National Phase application under 35 U.S.C. § 371 of International Application No. PCT/EP2014/052955, filed on Feb. 14, 2014, which claims the benefit of European Patent Application No. 13155428.9, filed on Feb. 15, 2013.These applications are hereby incorporated by reference herein

FIELD OF THE INVENTION

The present invention relates to an X-ray apparatus, to a method of correcting a field of view setting of an X-ray apparatus, to a computer program element and to a computer readable medium.

BACKGROUND OF THE INVENTION

Medical personnel in intensive care units or in A & E (Accident and Emergency) departments have come to rely more and more on mobile X-ray imagers. They afford acquisition of X-ray images even under awkward, adverse conditions. For example elderly patients in care homes who have been bed-ridden for long will need to have a chest X-ray taken every day to monitor for possible build-up of water in their lungs which could lead to pneumonia. It has been however noted that, although some of those mobile X-ray imagers are equipped with devices (such as collimators) to help keep dosage down, X-ray dosages for patients and personnel were still surprisingly high. A mobile X-ray imager is described in Applicant's WO2008/023301.

A particular problem in such apparatus is that it is difficult to determine an optimal setting for the collimator. Moreover, achieving a proper alignment of the X-ray source and the detector is cumbersome.

SUMMARY OF THE INVENTION

There may therefore be a need for an improved X-ray apparatus to address at least the above mentioned deficiency.

The object of the present invention is solved by the subject matter of the independent claims where further embodiments are incorporated in the dependent claims. It should be noted that the following described aspect of the invention equally apply to the method, to the computer program element and to the computer readable medium.

According to a first aspect of the invention there is provided an X-ray apparatus for image acquisition (also referred to herein as "imager"), comprising:

an X-ray source configured to generate X-ray radiation for image acquisition of an object;

a collimator configured to collimate the X-ray radiation into a radiation cone, said radiation cone irradiating the object at a region of interest when acquiring the image;

a portable radiation detector, the detector configured to register the X-ray radiation after passage through the object, a field-of-view corrector configured to receive, in a pre-shot imaging phase, a scout image acquired by the detector with a tentative setting of the collimator, resulting in a low dosage radiation cone impinging on the detector, the low dosage cone having in the detector's image plane a first cross section being smaller than a surface area of the detector, the field-of-view corrector being further configured to use said scout image to establish field-of-view correction information for a subsequent imaging phase, the field of view correction information including collimation correction information for determining a corrected setting of the collimator, wherein, in the subsequent imaging phase, the corrected setting of the collimator results in a high dosage radiation cone impinging on the detector, the high dosage being higher than the low dosage and the high dosage radiation cone having, in the detector's image plane, a second cross section being larger than the first cross section and the high dosage radiation cone i) being essentially coextensive with the surface area of the detector or ii) being a symmetric enlargement of the first cross section and extending in its entirety within the surface area of the detector.

During preparation of an imaging session, the X-ray source, patient and the portable detector must be set up properly. However, it has been found that the patient often covers the detector fully. As a result, it had been difficult to select the correct setting for the collimator.

According to the invention, a correct setting of the collimator can be determined more accurately. A pre-shot is applied at a small tentative collimator setting, resulting in an exposed field being much smaller than the detector. By determining, for this pre-shot, the cross-section and position on the detector, one can calculate an optimal setting for the collimator to be used during subsequent imaging, based on the known tentative collimator setting.

In a preferred embodiment, only a single scout image is acquired and the subsequent imaging phase can proceed with the immediate next image (that is, imager than operates with the high dosage cone to acquire said next image) after the scout image acquisition. However on occasion more than one scout images may be acquired so in this embodiment the high dosage subsequent image phase commences after acquisition of more than one scout-images. The user may then select on which one of the more than one scout images the operation of the corrector is to be based.

The dosage at which the imager operates to acquire the scout image in the pre-shot phase is deliberately lower than the higher dosage for acquisition of the follow-up image in the subsequent, "proper" imaging phase. Given a certain minimum image contrast to be achieved, said higher dosage is a function of the patient's thickness in direction of passage of the radiation cone through the patient. The higher or "right" dosage can be obtained from tables or databases and/or from evaluating the scout (or pre-shot) image. But, rather than using the pre-shot image merely for determining the right dosage for the instant patient, the X-ray apparatus FoV corrector further harnesses the image information in the pre-shot image to adjust the field-of-view settings to so achieve proper collimation and, optionally, tube-detector alignment. In other words, the apparatus's corrector put the pre-shot image to new use, namely field-of-view correction. To still use the pre-shot image on top of the FoV correction for the dosage determination is, of course, not excluded and is indeed envisaged herein by some embodiments.

The X-ray apparatus is in one embodiment is of the mobile type. This means in particular that its detector is portable (or "mobile") so is not permanently coupled to the X-ray tube during the image acquisition. In one embodiment the whole apparatus is mobile in that it includes a mobile frame or undercarriage (with rollers or similar) to so allow use in different locations, in particular in different rooms of a ward or similar although, for example, ceiling-mounted constructions are also envisaged herein.

In other words the apparatus as proposed herein has a functionality to obtain the field of view correction information using a very small low dosage pre-shot image. This can help to bring down the dosage for both personnel and the patients. This is because it has been observed that medical staff frequently use maximally opened up collimation settings when acquiring X-ray images. The practice of using a collimator setting with maximum aperture provides a good chance that the region of interest is actually captured in the image. However, this comes at the expense of increased dosage. It has been observed that staff is more likely to use maximum collimation in mobile X-ray imagers where the mobile detector is not normally visible during the pre-shot because, for example, the patient lies on same and because the alignment between tube and detector is not known to the required precision because of the portable nature of the detector. It is therefore difficult for the staff to guess a good initial field of view setting for the pre-shot image. The X-ray apparatus with the mobile detector as proposed herein helps take the guess work out of arriving at optimized field of view settings and, in particular, optimized collimator settings.

The apparatus can be used with symmetric or asymmetric collimators and embodiments for either collimator type are envisaged herein.

According to one embodiment, the corrector uses the scout image to compute the imager's SID (source to image-receptor distance, i.e. the distance between X-ray source and detector) when establishing the collimator correction information.

According to one embodiment, the corrector uses the scout image to compute a deviation between i) a position where the low radiation cone's central beam irradiates the detector surface and ii) the center point of the detector surface area to so establish off-center information.

According to one embodiment the X-ray apparatus includes a graphics display controller to render the correction information for display on a screen, the correction information when so displayed suitable to guide a user to manually change the imager's SID and/or the X-ray tube's position in a plane parallel to the detector's image plane to so carry the field-of-view correction into effect.

According to one embodiment the X-ray apparatus includes a collimation controller configured to use the established field-of-view correction information to apply said correction information to the current tentative collimator setting to so automatically effect the corrected collimator setting for the subsequent imaging phase.

According to one embodiment, the application of the field-of-view correction operation results in the high radiation cone being centered relative to a center point of the detector surface area, the collimation controller operative to use the off-center information to adjust at least one of the collimator's movable shutters.

According to one embodiment, the X-ray apparatus includes an X-ray tube position controller configured to use the off-center information to effect moving the X-ray source in a plane parallel to the detector's image plane so as to effect a radiation cone centration operation.

According to one embodiment, the collimator is of the asymmetric type and the centration of the X-ray beam may be effected without moving the X-ray source , by independently moving the individual shutters of the asymmetric collimator. This allows optimizing FoV even when no motion of X-ray tube is possible or it motion is not desired.

Definitions

"Radiation cone" as used herein refers to the shape of the volume between collimator aperture and detector surface that is irradiated or "flooded" with mostly primary radiation. "Cone" is used herein in the broad mathematical senses, so in particular includes not only the classic circular cone but also a pyramid. In particular, cone as used herein is not meant to restrict the present apparatus to "cone beam" imagers (a terminology frequently used to distinguish for instance from fan beam imagers etc).

"Cross section" of the radiation cone in the detector image plane is the irradiation field or FoV formed by the radiation cone in the plane defined by the detector's radiation receiving surface.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
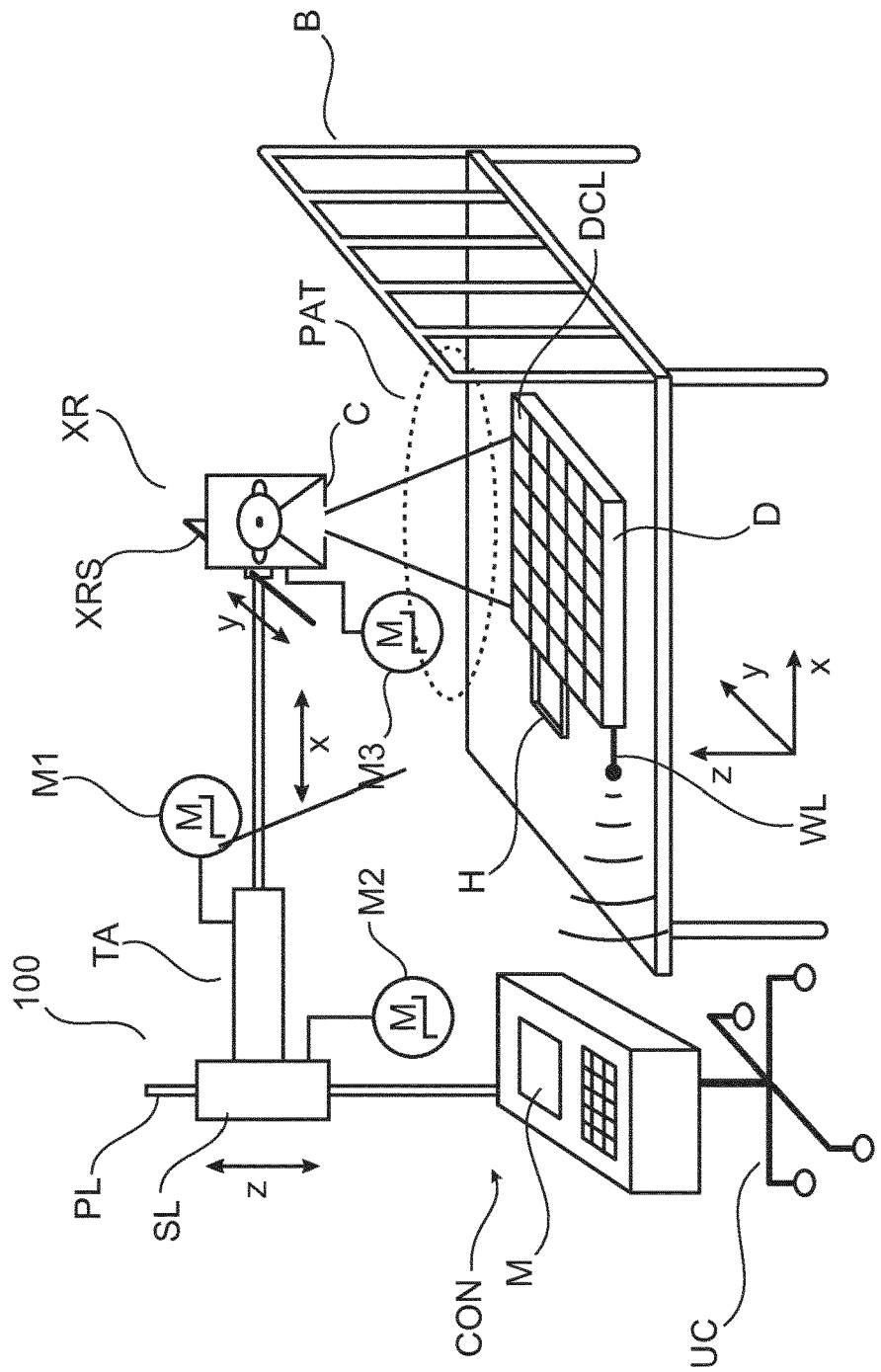
FIG. 1 shows an arrangement using a mobile X-ray apparatus.

With reference to FIG. 1 there is shown a mobile X-ray apparatus 100. Mobile X-ray apparatus such as the one shown in FIG. 1 may be used in intensive care wards of in A&E.

According to one embodiment apparatus 100 is of the "dolly type" and comprises an undercarriage on rollers so as to be position-able at a convenient position relative to the patient PAT. There is an operator console CON for clinical personnel (in the following referred to as operator) for operating imager 100. Operator can control via said console OC image acquisition by releasing individual X-ray exposures for example by actuating a joy stick or pedal or other suitable input means coupled to said console CON.

The console also includes a display unit M for viewing acquired X-ray images or for displaying a user interface to guide the operator when using the X-ray at the mobile X-ray apparatus 100. In one embodiment the console CON merely comprises the monitor M. According to one embodiment the mobile X-ray apparatus 100 includes an X-ray positioning mechanism. Said mechanism allows movement of an X-ray tube XR substantially in horizontal plain x,y and, in some embodiments, also perpendicular thereto in a z direction. Said tube positioning mechanism is movable relative to the X-ray apparatus undercarriage UC.

X-ray tube XR is arranged in a housing which also includes a collimator to collimate radiation egressing from said X-ray tube XR ("tube").

According to one embodiment the tube positioning mechanism includes an essentially upright pole like member PL which includes a track slider SL slidable in z direction along said pole. The tube collimator housing is coupled to the said slider SL via a telescopic arm TA. Slideability along pole PL affords adjustment in z direction, whereas the telescopic arm TA allows positioning X-ray tube, and with it the collimator C, in y direction. There is a further slider mechanism XRS that allows slideability in y direction perpendicular to the y direction. Both sliders can be arranged as ball-bearing units with rollers that are received in respective tracks but this is but one example and other mechanical solutions are also envisaged. Movement in z-direction may not necessarily be vertical. For instance, patient may lie slightly tilted in bed B, e.g., with shoulders higher than pelvis. In this case the whole X-ray apparatus or pole member PL may be tilted around a pivot point (not shown) to compensate for patient's posture.

As shown in FIG. 1 the housing includes handles for manually positioning the position tube XR in space. However a motorized embodiment is also envisaged in which there are arranged a number of suitable mechanical actuators M1-M3 such as stepper motors or the like via which movement along the respective axis x,y,z can be independently effected.

As shown in FIG. 1, there is also a mobile or portable detector unit D.

In one embodiment the detector D is a relatively flat, slab or plate-like object and includes an array of detector cells DCL sensitive to receive the radiation emitted from the X-ray source that are attenuated by parts of the patient's body as will be described in more detail below. In one embodiment detector unit D is rectangular in shape measuring about 30 cm×40 cm in the x,y plane with a thickness in z direction of about 3-5 cm or less. The mobile detector may be a film cassette or a fully digitalized unit. The detector D is capable of communicating with the X-ray apparatus operating console via wireless connection. The console and the mobile detector include suitable wireless interfaces WL to do this.

Although less convenient in most cases there is also a wired embodiment envisaged where the detector D communicates via wired socket connection. The mobile X-ray apparatus including its mobile detector can be used by the operator (e.g., a radiographer), for example in support of a physician doing his or her daily rounds in an intensive care unit. In use, the physician would grab the pole like structure PL of the mobile X-ray 100 and "roll it over" via the rollers of undercarriage UC to position imager 100 close to bed B where the patient PAT lies.

The patient is then asked to sit up or, if to infirm to do so, is gently rolled over by medical care staff and detector plate D is positioned on the bed's B support surface. In one embodiment portable detector unit D includes a handle H to facilitate its positioning. The patient PAT is then either rolled over or asked to lie down so as to cover essentially with their chest or back or other regions of interest the portable detector D. To make this experience more convenient for the patient it is also envisaged in one embodiment that the mobile detector includes heating elements arranged across its surface so as to ensure said surface is essentially close to body temperature when the patient PAT's body contacts the detector D surface when lying down. One possible clinical application is chest X-ray. However it is envisaged that the apparatus may be likewise put to good use in A&E when an X-ray needs to be taken of other body parts such as the patient's hand, foot, leg or head if an examination for injuries is called for.

As can be appreciated from the above scenarios, but in particular in the chest X-ray scenario, large parts (or even the whole) of the X-ray detector's radiation sensitive surface itself may not actually be visible during the imaging because the patient is lying on it. Detectors come in various sizes and, for example, a rather compactly built detector may completely "vanish" out of sight when a rather corpulent patient is asked to lie down on same.

In other words, if the operator were to proceed with the actual image acquisition after a rough-an-quick X-ray tube-patient alignment, there is a serious risk of obtaining sub optimal images because the detector and X-ray tube/detector and collimator are likely to be misaligned or misadjusted, respectively. The danger of misalignment is aggravated by the mobile nature of the imager 100, that is, there is no permanent, pre-defined and a priori known spatial relationship between X-ray tube/collimator and the detector's image plane as would be the case, for example, in a C-arm imager where detector, collimator and X-ray tube are permanently mounted in opposed relationship on the respective ends of the C-arm.

Figure 3:
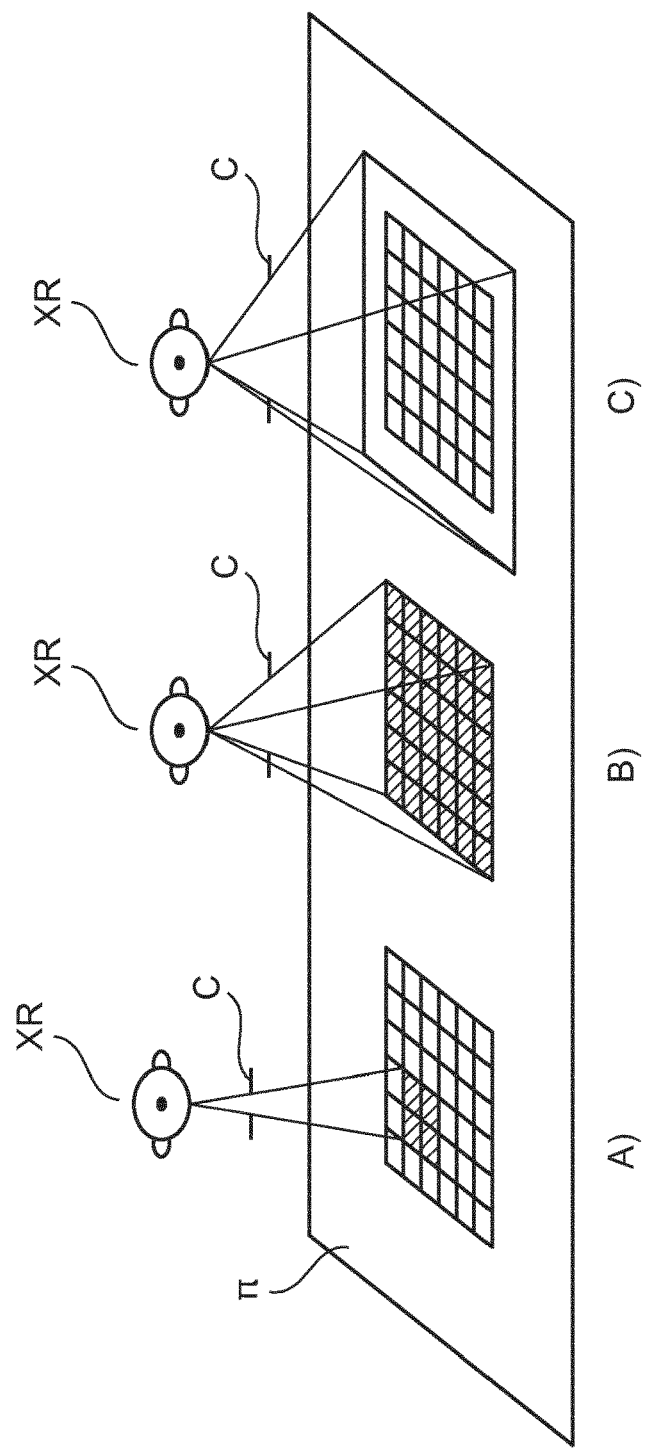
FIG. 3 shows various exposures of a detector to different radiation cones.
Figure 4:
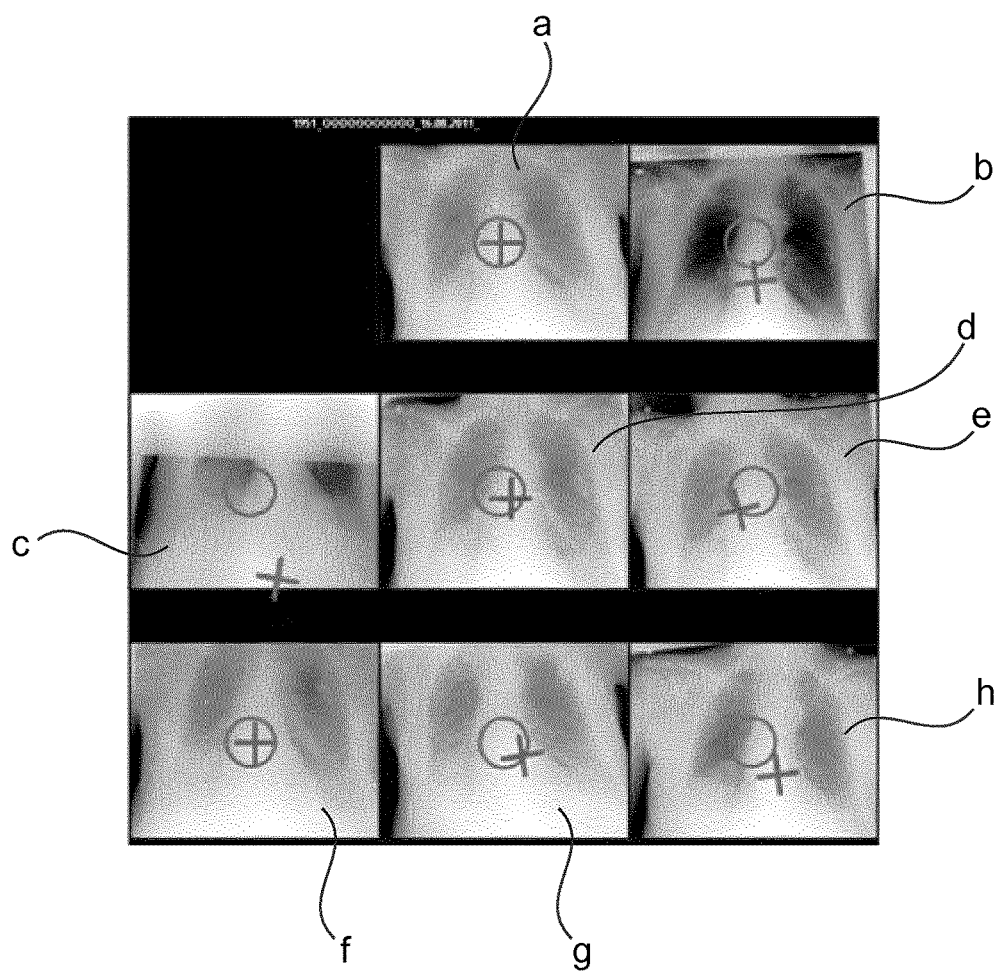
FIG. 4 shows different X-ray images acquired with different field of view settings.

The following FIG. 4 shows what can go wrong. The tiles in the 3×3 picture array show examples of X-ray images using a conventional mobile X-ray apparatus. The examples evidence certain collimator maladjustments. Circles indicate the respective center portion of the detector surface. For example, for a rectangular detector image surface said position is defined as the intersection of the two diagonal lines. The cross symbol on the other hand demarks the center of the field of view or collimation aperture/window for a given SID and exposure. More details on field of view (FoV) settings (which include collimator settings, that is the size of collimator's aperture used in the exposure) and its geometry will be explained in more detail below with reference to FIG. 3. Referring back to FIG. 4, tile a) shows the desirable situation where the center of the collimator's field of view and the center of the detector image plane coincide. Although not as good as a), tile f) shows a situation that may still pass as acceptable in some medical cases. However tiles b)-e), g) and h) evidence stark misalignment, especially tile c) which is "cut-off".

In order to take the guess work out of image acquisition with mobile X-ray, the present mobile-ray apparatus as proposed herein includes a module MOD that helps the operator to gain the necessary clue on the mutual spatial relationship between X-ray tube/collimator and the mobile detector at very low dosage cost.

Figure 2:
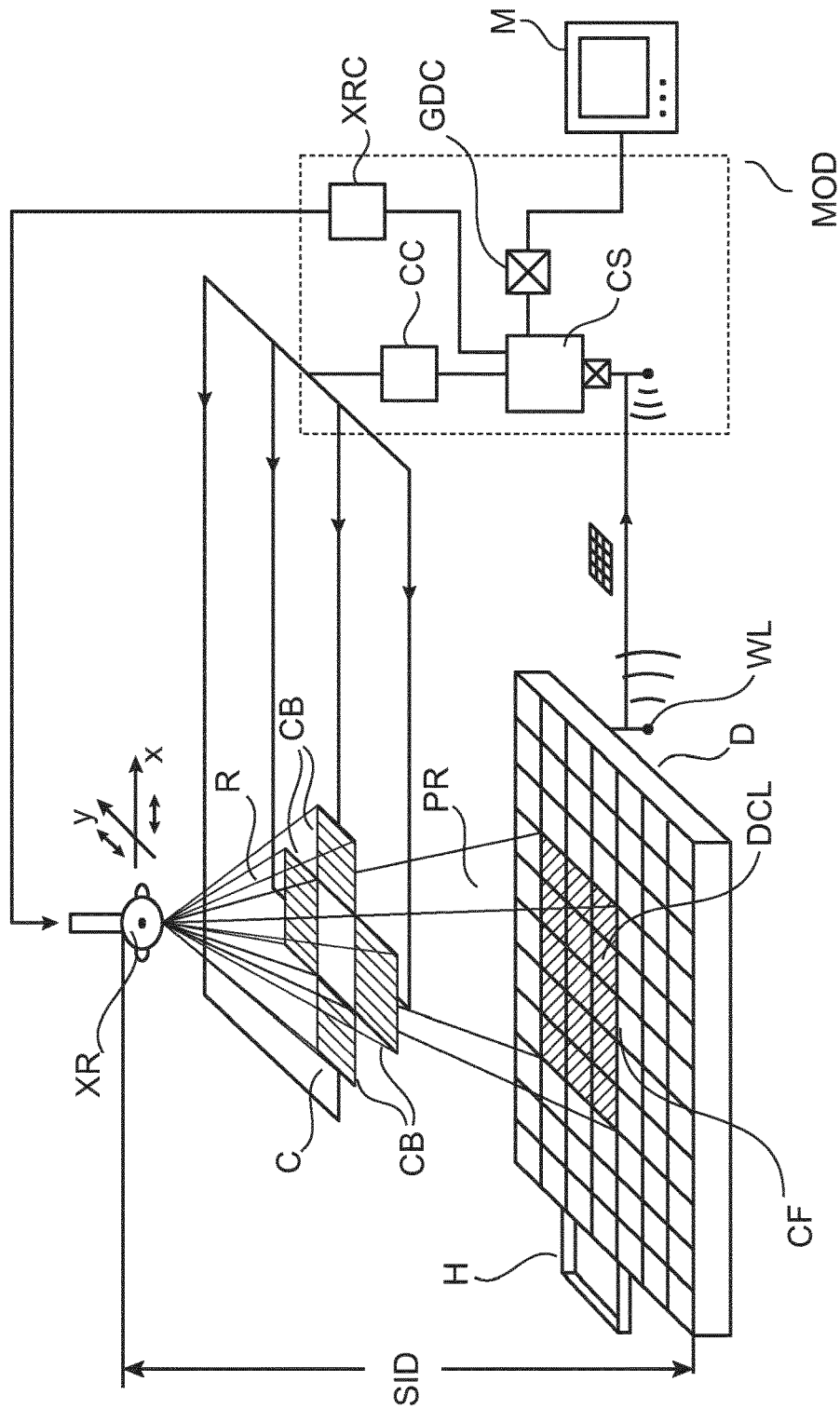
FIG. 2 shows a more detailed and partly cut-away view on the X-ray apparatus in FIG. 1 including a module.

Reference is now made to FIG. 2 that affords a partly cut-away view of the components of the imager and which serves to lay bare the functioning of the module as proposed herein. The module MOD includes a field-of-view setting determiner/corrector CS. According to one embodiment there is a collimation controller CC. In a further embodiment there is an X-ray tube positioning controller XRC. In one embodiment there is also a graphical display controller GDC.

The left hand side of FIG. 2 is a partly cut away view on the X-ray tube XR, collimator C and mobile detector D. To better show the imaging geometry, patient PAT is not shown. Radiation egresses the X-ray tube as radiation cone R and ingresses collimator C. The purpose of collimator C or "beam restrictor" is to restrict dimensions of the cross section of cone PR so as to match in size and shape a region of interest ROI. Collimator C comprises, according to the embodiment in FIG. 2, two pairs of blades CB or sheets ("shutters") formed from lead or tungsten or other highly radiation-opaque material. One pair is arranged perpendicularly to the other and the blades are individually addressable and movable by a respective collimator stepper motors (not shown) so as to restrict more or less the radiation cone in either or two of the two dimensions depending on their relative position. Blades CB may be rotatable and/or shiftable in and out towards a center formed by the four blades. The collimator arrangement in FIG. 2 allows shaping the beam into square or rectangular forms in various sizes. In another embodiment a multi-leaf collimator is used comprising instead of the four blades a large number of motor-movable slats or strips arranged in opposing relationship. A multi-leaf collimator allows forming more detailed, e.g., curvilinear shapes. Each collimator setting or configuration corresponds to a specific position of blades BC forming the collimator aperture shown in FIG. 2 bounded by the four blades. Because of the high radiation opacity of blades CB, primary radiation come PR incident on the blades CB is blocked whereas that part of radiation cone PR that is directed at the aperture is not blocked so can pass collimator C to irradiate patient PAT volume in a target volume.

Broadly, during an image acquisition the collimated X-ray beam PR emanates from X-ray tube XR, passes through patient PAT at said region ROI, experiences attenuation by interaction with matter therein, and the so attenuated cone PR then strikes detector D's surface at a plurality of the detector cells. Each cell that is struck by an individual ray (of said primary cone PR) responds by issuing a corresponding electric signal. The collection of said signals is then translated by a data acquisition system ("DAS"—not shown) into a respective digital value representative of said attenuation. The density of the organic material making up the ROI, for example rib cage and cardiac tissue, determines the level of attenuation. High density material (such as bone) causes higher attenuation than less dense materials (such as the cardiac tissue). The collection of the so registered digital values for each (X-)ray of cone PR are then consolidated into an array of digital values forming an X-ray projection image for a given FoV setting.

As mentioned, after passage through at least parts of the patient body the radiation cone PR is then incident on the detector's surface and excites certain of the detector cells DCL. Exactly which of the detector cells are excited by any given radiation cone is a function of i) the SID (X-ray-tube to detector distance) and ii) the size of the collimation aperture defined by the mutual positions of the blades CB. Collection of all detector cells excited by any a given (in this case collimated) cone CR defines a cross section in the detector's image plane whose shape is the central projection of the collimation aperture with the X-ray source at the center of the projection. The field (or for that matter the image) has a boundary B. In the embodiment of FIG. 2, this is the perimeter of a rectangle owing to the rectangular/square collimation aperture). Geometrically, the irradiated field CF may be understood as the cross section of the radiation cone PR formed by intersecting x,y plane π (see FIG. 3) defined by the detector D's surface. Ideally, the whole of said cross section field CF lies within the detector D's surface as shown in FIG. 2. Undesirably, this may not always be so however is indicated earlier in the chest X-ray example, particularly when mobile detector units are used, as the X-ray image in tile c of FIG. 4 evidences: if some the cone's cross section is outside the detector D's surface, the image appears "cut-off". This is very undesirable, because part of the anatomic information has been lost, but dosage has still been incurred for both patient and staff. Ideally, image plane it is parallel to the plane defined by the supporting surface of bed B on which the patient and the detector lies during the image acquisition. If not, detector D is tilted, the amount of tilt being definable and quantifiable by suitable angular quantities/measurements.

As shown in the Figure the actual FoV for any exposure is given a) by the size of the cross section and or shape thereof and b) the position of the exposed area CF within the detector surface. Collimator's aperture can be gradually increased (given a step Size of the blade actuators) from completely closed to a maximum collimation window or aperture.

Briefly, for an imaging session, operation of the X-ray apparatus module as proposed therein proceeds in two consecutive phases: in a pre-shot phase and in a subsequent image acquisition phase. In the pre-shot phase a scout image SI is acquired where the X-ray radiation tube operates at a much lower dosage, for example 5% of the actual dosage needed for the instant patient PAT under examination. In contrast to previous systems the scout image is very small, typically in the region of 50%-60% of the whole detector surface area.

In one embodiment, the dimension of the scout image are 50% of detector D's extension d in x-direction and 50% of detector D's extension h in y-direction, resulting in 25% of the detector D's area. In the FIG. 5 embodiment, the size ratio is about 30%. In other words no maximum collimation aperture is used for the pres-shot scout image.

Figure 5:
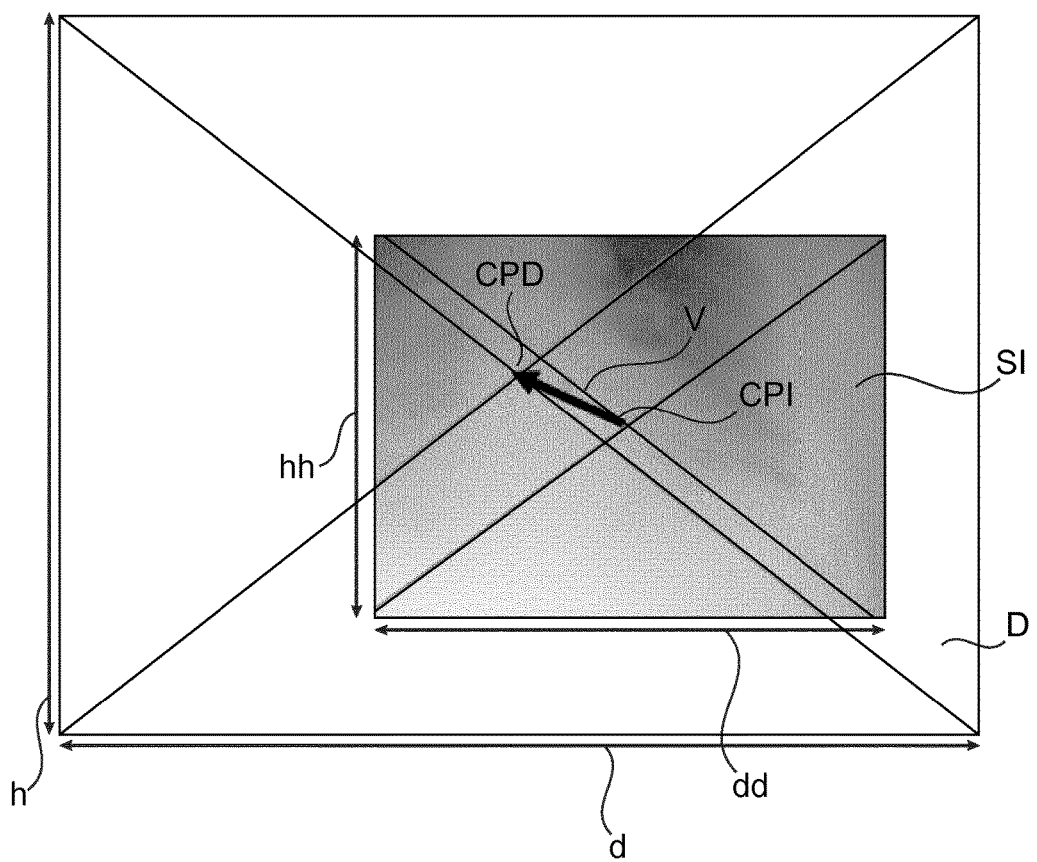
FIG. 5 schematically shows a graphical user interface.

The geometric center of the scout image SI is compared with the a-priori known center of the detector D surface. This operation is indicated in FIG. 5. A deviation vector V can be established that allows component-wise resolution of the deviation in x and y direction. The so established deviation vector ("off-center information") measures the extent to which the scout image SI is "off-center" relative to the detector surface's center point. Other FoV information which can be extracted from the small scout image SI is measuring the area size of the scout image (by establishing length and width, that is, the image's extension in x,y direction) and establishing the ratio therewith to the total area detector D surface. This ratio can be used to establish the correct SID. More specifically, to compute the SID the collimator C's opening cx and cy are compared with scout image extensions hh and dd. Given the FCD (focus-collimator distance), the SID=FCD*dd/cx or SID=FCD*hh/cy, it being understood that this refers to the rectangular collimator embodiment and that corresponding size parameters are to be used for collimators with other aperture shapes. The correct SID is taken to mean the distance between the X-ray tube and the detector surface image plane at which the size of the scout image (that is, the cross section of its planar radiation field CF) would exactly correspond to the size of the detector surface.

As will be appreciated, the SID for the pre-shot is not exactly known before the pre-shot but can only be roughly estimated by a way of a length gauge that is run along pole element PL. However, after evaluation of the pre-shot scout image SI, the SID is known as explained above in the previous paragraph. The initial aperture size (usually 50%-60% of maximum aperture) can then be roughly estimated so that the scout image SI as registered by detector D will indeed be "small".

Briefly, after acquisition of the scout image in the pre-shot phase, the image is then forwarded via wireless connection from a wireless transmitter of the mobile detector to a wireless receiver at the module. The collimation setting corrector then uses in the previously described manner the image information in the scout image (in conjunction with the a priori known center point and total surface area of the detector) to establish the deviation vector and/or the correct SID. From the correct SID, the correct collimation aperture can be computed.

The FoV correction information can then be forwarded in one embodiment to collimation controller CC. Collimation controller CC is in communication via suitable interfaces with collimator C to control movement of the collimator blades to so readjust the collimation aperture to open up so that, in a follow up image, the radiation cone cross section is essentially coextensive with the detector's surface area. The correction information may also be forwarded in one embodiment to an X-ray tube position controller to center the tube XR, by shifting same in the x, y plane, over the center point of the detector surface. This allows, for a follow-up exposure in the subsequent imaging phase, to produce a radiation cone whose center beam will impinge the detector substantially at the detector surface center point or, within a user definable allowance margin, around said detector surface center point.

According to one embodiment collimator C is of the symmetric type. In other words the opposite collimator blades cannot move independently from each other but are always moving together thereby ensuring that the shape of the aperture remains the same no matter the size of the aperture. This can be achieved by coupling each of the collimator blades via a suitable gearing mechanism so that the blades move together in a synchronized fashion to maintain a symmetric aperture for any desired setting.

In another embodiment the collimator is of the asymmetric type. In such a collimator each of the blades can be moved individually and independently from each other. Also an asymmetric collimator affords effectively shifting the collimation window across the detector's image plain by moving only one pair of opposing blades in the same direction. The collimator of either type may be either fully automatic, semi automatic or manual. In the manual embodiment X-ray apparatus includes mechanical actuated means such as levers or thumb-wheels or similar mechanical means to manually effect and control the motion of the collimator blades.

In the semi automatic embodiments there are server motors or other actuators which are energized upon the user pressing suitably marked up buttons to so request motion of the collimator blades CB.

Finally in the fully automatic embodiment the blades are responsive to collimator controller CC that issues control commands upon receiving collimator correction information. In other words, in the fully automatic embodiment no user interaction is required during the motion of the collimator blade CB.

According to one embodiment the actual apparatus also includes an anti scatter grid to block out secondary radiation that is caused Compton scattering ("secondary radiation") as the primary radiation cone RC passes through the patient which compromises image quality. In order to minimize the amount of secondary radiation impinging on the detector cell surface an anti scatter grid is positioned between patient and detector surface. According to one embodiment the grid is either permanently installed on top of the detector surface but is removable. Removable scatter grid (not shown in the Figures) is closed for example snap-fitted onto the mobile detector via a number of pins. According to one embodiment the detector and/or the entire scatter grid may include detection means in order to detect whether there is an anti scatter grid mounted.

In a simple embodiment the anti-scatter grid essentially a grid-like structure formed from small fins extending away from and perpendicular to detector surface. The grid when mounted covers essentially all the detector surface. The grids mounting pins are partly metallic and are received in corresponding recesses in the detector housing. Once received therein, an electric circuit is closed whereupon a logic circuitry sets a certain flag. The flag indicates that, if set, the anti scatter grid is mounted and, if not set, that no anti scatter grid is mounted. In another embodiment, RIFID sensors are used instead for grids and detectors. This allows not only for grid presence detection ("a grid is used") but also to query the grid type ("which grid is used"),In some embodiments, when the scout image is established to be off-center, as will be explained in more detail below, the presence of the grid is queried by corrector in relation to the decision on whether or not to shift the X-ray tube or whether or not to indicate to the user the X-ray the tube be shifted. According to other simple embodiments the apparatus may simply include a switch that can be toggled between two positions to indicate whether or not the anti scatter grid is used.

Very briefly, the module MOD as proposed herein operates via its field of view setting determiner CS to determine corrected FoV settings based on the information in the small scout image.

In a basic embodiment the established FoV correction information is merely displayed on the monitor as to guide the user to manually effect the correction. The graphics display controller GDC renders the information in suitable form on screen. For example FIG. 5 shows one embodiment of such a display. Displaying said FoV correction information can be used in particular with the previously mentioned semi automatic and the manual embodiments of the imager. The user interface includes a graphic representation of the detector surface D (in the FIG. 5 likewise indicated by numeral "D") with detector width d/height h and a second window indicating the size of the scout image SI having width dd/height hh. Respective center points CPI, CPD of scout image SI and of detector surface is likewise indicated by suitable markers in the graphics display. In this embodiment the markers are indicated on the intersecting diagonal lines of the respective frames. The off-center information, is indicated by a vector V. The graphic user interface may be interactive in that once the user is changing the field of view settings the vector is likewise changing to indicate progress of approaching the correct centration. In the embodiment in FIG. 5, of-center vector V would change its direction and would change its size, for example would eventually shrink to a point, to indicate that the correct center point CPD has been reached. In another embodiment however another graphical indication may be used such as that shown in FIG. 4, where the center of the detector is shown as a circle for instance and the center of the scout image is indicated as a cross hair symbol. In this embodiment, positions of cross and circle would be interactively updated according to the user changing the field of view settings. The correct centration is reached once the cross is entirely positioned within the circle. However, other graphic widgets may be used to the same effect and the skilled reader will understand that the previously described embodiments for the graphic user interface are purely for illustrative purposes.

Operation of the module will now be explained in more detail below.

Operation

The, relative to the total detector D surface, small scout image SI is received, preferably via wireless communication, at the module's interface or input port and is then forwarded to the field of view setting determiner CS. The determiner CS then operates to establish the off-center information by comparing the respective center points of the scout image and the known center point of the detector surface. As explained earlier, the in-image plane vector V as shown in FIG. 5 can be established to measure the deviation.

In one embodiment, field of view determiner CS operates to establish the desired SID. To this effect, and as indicated earlier, the ratio of the area sizes of detector surface and scout image is established. The ratio number then allows adjusting the tentative SID that was chosen when the scout image was acquired. Once the SID is known, an, in general, enlarged maximum collimator aperture can be computed that would produce a radiation cone whose cross section is still completely within the detector surface area. In particular, the information on the correct SID can be combined with the off-center information to so arrive at a collimation aperture that will produce a cone whose cross section is essentially coextensive with the total detector surface area. This enlarged collimation aperture can be computed from the computed SID on geometric grounds by an application of the intercept theorem.

Field of view correction determiner CS may also operate to establish, if any, a tilt between the detector surface and the reference plane given, for example, by the support surface of the bed on which the patient lies during the image acquisition. The amount of tilt can be measured by establishing distortion in the scout image. For instance, if the collimator aperture is a rectangle then the scout image is likewise a rectangle under correct perspective projection. If there is tilt, there will be perspective distortion which can be measured by the angles formed at the scout image's vertices. In the rectangular aperture collimator embodiment, the scout image will be distorted to assume a trapezoidal shape due to the tilt. Therefore the angles will be less than 90°. The amount by which the angels fall short of 90° can be then be used to quantify the tilt. It will be appreciated that the determiner CS may not in each and every embodiment compute all the three field of view settings i) off-center deviation, ii) SID/collimator aperture and iii) tilt. For instance, the tilt may be ignored in some embodiments and it is only the centration and collimation window size that is established. In other embodiments however it is only the centration that is established and not the desired updated collimation aperture/SID.

FIGS. 3A, B show schematically the effect of the proposed module MOD on the imaging geometry in one embodiment. Figure A shows the situation in the pre-shot phase where the small (relative to the detector size) scout image SI is acquired with low dosage at the tentative field of view setting, including a tentative SID and collimator aperture. As can be seen in FIG. 3A, scout image SI is slightly off-center. The correction determiner CS establishes the corrected field of view settings. The field of view is then readjusted by effecting, via controllers CC, XRC, a planar shift of the X-ray tube in the x,y-plane and by opening up the collimator aperture.

In a subsequent imaging phase shown in FIG. 3B, a "proper" image is acquired with the patient-appropriate dosage and now using the corrected FoV settings with the image now being properly centered over the detector center and the image being essentially co-extensive with the detector surface.

The situation shown in FIG. 3C is the one to be avoided and is shown here for clarity. In scenario 3C, an image is acquired at "over collimation". As can be seen, the cross section of the radiation cone in the image plane π is larger than the detector surface so, in particular, extends beyond image surface. The situation is to be avoided because it incurs unnecessary radiation doses on both operator and patient.

In other words, in one embodiment and shown in FIG. 3A, in the pre-shot phase the pre-shot image or scout image SI is acquired by producing a low dosage radiation cone that irradiates only a small portion on the detector surface. After establishing by corrector CS the field of view corrections, the imager can then operate as shown in FIG. 3B with a higher dosage radiation cone which, when used for subsequent images, will intersect the image plane at a cross section now co-extensive with the detector's overall surface.

The pre-shot or scout image SI is acquired according to one embodiment with a 20 cm×20 cm collimation aperture or with a 10 cm×10 cm or 20 cm×10 cm collimation aperture but will depend on the size of the detector D. The "low" pre-shot dosage is established for the patient at hand by querying a data base where dosage values for patients according to sex, height, weight etc is tabulated. Said ideal dosage value is then scaled down to 5% for the pre-shot image SI.

Correction determiner CS operates to compute from image SI the length of its two edges in x,y direction. The overall area size of the scout image SI as recorded by the detector is then used to calculate the source distance, and, in one embodiment, the amount of tilt in degrees if desired by the operator. The SID that would afford the co-extensive exposure is then established and so is the deviation V from the center position.

According to one embodiment as mentioned earlier the tilt can be ignored. In the fully automatic embodiment, X-ray position controller XRC is instructed by corrector CS to energize the respective actuators to set the X-ray tube into lateral motion to assume the calculated center position. Corrector CS also instructs collimator controller CC to energize collimator blades CB to form the calculated collimation window. In one embodiment, the tube is moved into the calculated position after adjustment of the collimator blades. However the opposite order is also envisaged in some embodiments. The center beam of the radiation cone is now positioned more or less exactly above the center point of the detector surface.

Optionally, the z position of the tube XR can be adjusted also or is adjusted instead of changing the collimation aperture. Once the new X-ray XR and blade CB positions are assumed, a visual or acoustic "ready" signal may be issued to the operator. The imager is now ready to release an exposure that would afford the co-extensive irradiation of the detector surface in the next image. The user can then either instruct the imager to acquire the follow-up image using those parameters or he may now decrease the collimator aperture to a desired size or he may request such a decrease.

In an embodiment, where collimator C is asymmetric, the collimation aperture can be changed to effectively shift the radiation field across the detector's surface. In other words, the centration of the cone with respect to the detector surface center point can be achieved without moving the X-ray tube XR. The user can select whether a centration with our without tube XR motion is desired.

In an embodiment where the detector D tilt is accounted for, the new center tube position can be calculated in the tilted detector coordinate system.

In one embodiment with symmetric collimator, no re-positioning of the X-ray tube in the x,y plane is desired or such a tube re-positing is not possible. In this embodiment, the corrector CS queries the flag for the presence of the anti-scatter grid. If it is detected that there is an anti scatter grid and if the correction determiner reveals that the current X-ray position is off-center, a corresponding visual (for instance on the graphics display of screen M) or acoustic alert message is generated to the user. The user can then still decide to readjust the X-ray position or have it readjusted. If it is detected that there is no anti scatter grid, the off-center information, if any, may still be indicated to the user on the screen. If however the collimator is only of the symmetric type, the corrector CS operates to establish the field of view correction information as the maximum collimation window that would, when used, produce a cone whose cross section would still entirely fall within the detector's surface. More specifically, and for the embodiment with the rectangular aperture collimator, this would amount to compute an aperture so that all four edges of the rectangular radiation field of the radiation cone would still fall into the detector surface. If the collimator is of the asymmetric type, the radiation cone can still be centered as observed above.

In other words in this embodiment the off-center position is accepted at a cost of not being able to achieve a collimation with the entirety of the detector surface being irradiated.

In either of the embodiments, the pre-shot image or scout image can be used, in an otherwise known manner, to estimate therefrom the correct (in general higher) radiation dosage for the instant patient that is to be used for the follow-up images. The so proposed radiation dosage may then be displayed on screen M to the user who can then decide whether to accept the so calculated dosage or whether operator wishes to revert to the pre-defined calculated dosage as retrieved from the database. The apparatus in one embodiment allows the opportunity to override any of those values and to rather choose a different dosage altogether. "Proper" X-ray images can now be acquired in the imaging phase with the corrected field of view at a higher dosage than in the previous pre-shot phase.

It will be appreciated that the above distinctions of manual, semi automatic and automatic applies to the X-ray tube movement also. It will also be appreciated that the embodiment in FIG. 3 of the X-ray imager as shown in the dolly type is exemplary only. For instance, in a different embodiment a ceiling mounted embodiment may be used instead. This embodiment is still "mobile" in a sense that the X-ray tube can be positioned anywhere in the examination room and, in particular, there is still no permanent mechanical connection with the mobile detector. In this embodiment there is an overhead carriage fixed to a ceiling of a room. The overhead carriage has, in one embodiment, two perpendicular tracks, a first track being slidable over the second (fixed) track and the carriage having a suspension arm slidable in the first track. The suspension arm holds the X-ray tube which can then be positioned in any desired x,y position in the room. In this embodiment the suspension arm or the housing holding the collimator and X-ray tube will include a handle that allows the operator to "drag" the X-ray tube to the desired position. However, as will be appreciated, other mechanical mechanisms are also envisaged, so long as they afford shifting the tube XR at least in a plane parallel to the x,y plane of the detector D.

It may also be appreciated that in neither of the above embodiments it is necessary for the scout image to be complete. In other words a partial, "cut-off" scout image may still be sufficient to compute the field of view information as discussed above. A situation may occur when the initial adjustment of the X-ray imager relative to the patient was so badly chosen that the cross section of the radiation cone in the detector image plain is not completely enclosed in the detector surface but part of said cross section comes to lie outside it (see tile c) in FIG. 4). However in this case, because of the shape of the aperture is known the field of view information may still be computed. For instance, in the embodiment where the collimator aperture is rectangular it suffices if at least two of the image edges are recorded in full length. The area of such an incomplete "cut-off" scout image and the off-center information can still be extrapolated from this incomplete image for purely geometric symmetry reasons. In other words, as long as the recorded part of the image encodes enough of the complete image's symmetry, its center and total area can be recovered.

The X-ray imager's module is envisaged to reside on console/work station CON running as a software routine but in other embodiments may run on a processor integrated in the mobile detector unit D ("smart detector"). In yet other embodiments, a distributed architecture is used where module MOD or some of its components as of FIG. 2 run on a central computing unit rather than on the operator console CON. In this distributed embodiment, the module MOD may serve centrally a plurality of mobile X-ray imagers 100. The module MOD or some of its components may be arranged as dedicated FPGAs or as hardwired standalone chips. The module MOD may be programmed in a suitable scientific computing platform such as Matlab® or Simulink® and then translated into C++ or C (or other into suitable languages) routines maintained in a library and linked when called on by a processor.

Figure 6:
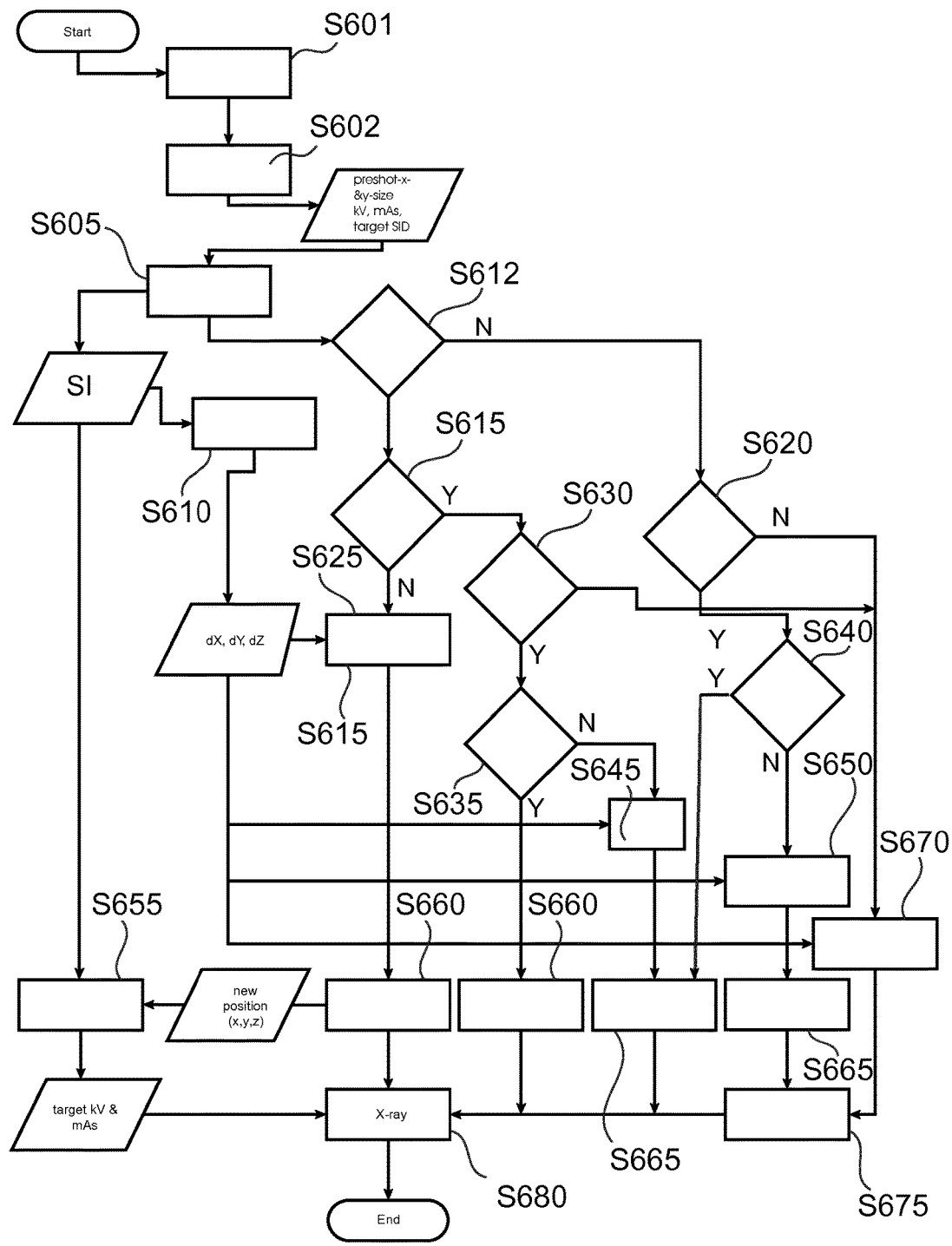
FIG. 6 is a flow chart for correcting field of view settings in a mobile X-ray apparatus.

With reference to FIG. 6 there is shown a flow chart for a method of correcting a field of view setting in an X-ray imager.

In step S601, a mobile X-ray imager is positioned relative to a patient and a mobile/portable detector is brought into position so that the patient is between the imager's X-ray tube and said mobile detector. A pre-shot image size (based on Collimator aperture size and an estimated SID) and corresponding kV, mAs and target SID values are then chosen as a tentative FoV setting. At step S602, a database may be queried to obtain these values. The X-ray dosage is chosen deliberately less than can be expected for the instant patient given a desired image contrast to be achieved.

In a pre-shot phase, in step S605, a pre-shot or scout image SI is then acquired using the tentative settings. Using the known geometry of the chosen collimator aperture, the exact size of the acquired pre-shot image and/or the exact SID and/or a maximum collimation aperture (in particular corresponding collimator blade positions) and/or off-center information is established at step S610. This can then be used for the centration of the imager's radiation cone. In one embodiment, the off-centre information is then displayed on a screen in steps S646, 650 and Step S670.

It is then established in step S612, whether collimator and/or X-ray tube are motorized.

If at least the X-ray is motorized, it is then established whether the collimator is of the symmetric or asymmetric type. If the collimator is of the symmetric type an X-ray positioning controller is instructed to energize respective actuators to re-position at S625 the X-ray tube according to the established off-center information.

In step S660 the collimator blades are then energized by one or more actuators as to form a radiation cone whose cross section in the detector image plane is essentially co-extensive with the full detector surface.

In the subsequent imaging/acquisition phase, "proper" follow-up X-ray images can be acquired at step S680 at a higher dosage using the so corrected field of view setting.

Previous to step S680, at step S655 the correct dosage is increased depending on the specifics of the current patient. In particular, the tube's kV, mAs values can then be adjusted and used in the subsequent imaging or acquisition phase. In one embodiment, computation of the mA values are based on image signals measured in the pre-shot scout image SI and a pre-defined target value, in other words the mAs value final for the subsequent imaging phase is final$_{mAs}$=preshot$_{mAs}$*target signal/preshot_signal.

If at step S612 it is established that, in particular, the mobile imager's X-ray tube positioning is not motorized it is then queried steps S620 whether or not there is an anti scatter grid in place.

If there is no anti scatter grid mounted, the off-center information is displayed on a screen at step S670 to invite the user/operator at step S675 to manually change the collimator setting (in particular its aperture) that would afford the largest collimator window without cutting off the image.

The follow-up image can then be acquired as previously at step S680.

If at step S620 it is established that there is a grid in place, it is then queried at step S640 whether the current field of view setting is off-center.

If it is established at S640 that the current field of view is not off-center or, if it established that it is still sufficiently central, the follow up "proper" image can be acquired at step S680 in the imaging phase.

If, however, it is established at S640 that the field of view setting is off-center, this fact is indicated at step s650 to the user. He can then, as previous, adjust at step S665 the tube position and/or manually adjust the collimator blades at step S675. The follow-up image can then be acquired at step s680. If at step S615 it is established that there is an asymmetric collimator available it is then queried in step S630 whether the anti scatter grid is in place.

If there is no anti scatter grid in place, the off center information can be displayed on the screen at step S670 to invite the user to manually move the collimator at step S675.

The follow up image can then be acquired at step S680. If it is established that an anti scatter grid is in place at step S630 it is then queried at S 615 whether the field of view setting is off center.

If there is sufficient centration, process flow then proceeds to step S660 where the collimator is energized to open up so that the imager is capable to produce a radiation cone whose cross section in the image plain is co-extensive with the detector surface as previously noted at step S660.

If, however, it is established that the current field of view setting is off-center, this fact is indicated at step S645 to the user and invited at step S665 to manually move the tube into a focal position according to the computed correction information. An image can then be acquired at step S680 as previously noted.

It is understood that in the previous method steps, operation of the collimator blades and/or the repositioning of the X-ray tube can instead be effected automatically if the query at S612 reveals that the instant imager has indeed the respective motorization. It should also be noted that the various displaying steps may also be skipped in some (fully) automatic embodiments. Preferably however and for safety reasons, the displaying step is executed even though the imager is automatic and is executed for manual and semi-automatic embodiments. It should be also noted that the previous steps include various query steps where a status of the imager is queried (gird yes/no, motorized yes/no, etc.). These steps afford a higher level of flexibility as the same program flow/method can be used for different type of methods. In some embodiments, if the method is tailed to a specific device, certain or all of the query steps can be skipped.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray apparatus for image acquisition, comprising:
an X-ray source configured to generate X-ray radiation for image acquisition of an object;
a collimator comprising at least one moveable shutter, the collimator being configured to collimate the X-ray radiation into a radiation cone, said radiation cone irradiating the object at a region of interest when acquiring an image;
a portable radiation detector configured to register the X-ray radiation after passage through the object; and
a field-of-view corrector configured to receive, in a pre-shot imaging phase, a scout image (SI) acquired by the portable radiation detector with a tentative setting of the collimator, the pre-shot imaging phase causing a low dosage radiation cone to impinge on the portable radiation detector, the low dosage radiation cone having in an image plane of the portable radiation detector a first cross section being smaller than a surface area of the portable radiation detector,
the field-of-view corrector being further configured to use said scout image to establish field-of-view correction information for a subsequent imaging phase, the field of view correction information including collimation correction information for determining a corrected setting of the collimator,
wherein, in the subsequent imaging phase, the corrected setting of the collimator results in a high dosage radiation cone impinging on the portable radiation detector, the high dosage radiation cone providing a higher dosage of radiation than the low dosage radiation cone, and the high dosage radiation cone having, in the image plane of the portable radiation detector, a second cross section that is larger than the first cross section and the high dosage radiation cone i) being essentially coextensive with the surface area of the portable radiation detector or ii) being a symmetric enlargement of the first cross section and extending in its entirety within the surface area of the portable radiation detector.

2. The X-ray apparatus of claim 1, wherein the field of view corrector uses the scout image to compute a source to image-receptor distance when establishing the collimator correction information.

3. The X-ray apparatus of claim 1, wherein the field of view corrector uses the scout image to compute a deviation between i) a position where a central beam of the low dosage radiation cone irradiates a detector surface and ii) a center point of the surface area of the portable radiation detector to establish off-center information.

4. The X-ray apparatus of claim 1, including a graphics display controller to render the correction information for display on a screen, the correction information when so displayed being adapted to guide a user to manually change the X-ray source to image-receptor distance and/or a position of an X-ray tube in a plane parallel to the image plane of the portable radiation detector, to carry the field-of-view correction into effect.

5. The X-ray apparatus of claim 3, including a collimation controller configured to use the established field-of-view correction information to apply said correction information to the collimator to so automatically effect the corrected collimator setting for the subsequent imaging phase.

6. The X-ray apparatus of claim 5, wherein an application of a field-of-view correction operation results in the high dosage radiation cone being centered relative to a center point of the surface area of the portable radiation detector, the collimation controller being operative to use the off-center information to adjust the at least one movable shutter of the collimator.

7. The X-ray apparatus of claim 3, including an X-ray tube position controller configured to use the off-center information to effect moving the X-ray source in a plane parallel to the image plane of the portable radiation detector to effect a radiation cone centration operation.

8. The X-ray apparatus of claim 1, wherein the X-ray apparatus is a mobile apparatus.

9. The X-ray apparatus of claim 7, wherein the collimator is an asymmetric collimator, and the at least one moveable shutter is a plurality of individual moveable shutters, and wherein the radiation cone centration operation is effected without moving the X-ray source but is effected by independently moving the plurality of individual movable shutters of the asymmetric collimator.

10. A non-transitory computer readable medium having stored thereon a computer program element, which when executed by a processor controls the X-ray apparatus according to claim 1.

11. The X-ray apparatus of claim 1, wherein the X-ray source operates at a lower dosage at the pre-shot imaging phase, and at a higher dosage at the subsequent imaging phase.

12. The X-ray apparatus of claim 11, wherein the lower dosage is 5% of the higher dosage.

13. The X-ray apparatus of claim 1, wherein the scout image is in a range of 50% to 60% of the surface area of the portable radiation detector.

14. The X-ray apparatus of claim 1, wherein the scout image is 25% or 30% of the surface area of the portable radiation detector.

15. A method of correcting a field-of-view setting of an X-ray imager, comprising the steps of:
receiving, in a pre-shot imaging phase, a scout image acquired by an X-ray apparatus with a tentative setting of a collimator comprising at least one moveable shutter, resulting in a low dosage radiation cone impinging on a portable radiation detector for acquiring the scout image, the low dosage radiation cone having in an image plane of the portable radiation detector, a first cross section smaller than a surface area of the portable radiation detector,
based on said scout image, establishing field-of-view correction information for a subsequent imaging phase, the field of view correction information including collimation correction information for determining a corrected setting of the collimator resulting in a high dosage radiation cone impinging on the portable radiation detector, the high dosage radiation cone having a higher dosage of radiation than the low dosage radiation cone, and the high dosage radiation cone having, in the image plane of the portable radiation detector, a second cross section that is larger than the first cross section, and the high dosage radiation cone i) being essentially coextensive with the surface area of the portable radiation detector or ii) being a symmetric enlargement of the first cross section and extending in its entirety within the surface area of the portable radiation detector.

16. A non-transitory computer readable medium having stored thereon a computer program element, which when executed by a processor, causes an X-ray apparatus to perform the method of claim 15.

17. The method of claim 16, further comprising operating an X-ray source at a lower dosage at the pre-shot imaging phase, and at a higher dosage at the subsequent imaging phase.

18. The method of claim 17, wherein the lower dosage is 5% of the higher dosage.

19. The method of claim 16, wherein the scout image is in a range of 50% to 60% of the surface area of the portable radiation detector.

20. The method of claim 16, wherein the scout image is 25% or 30% of the surface area of the portable radiation detector.

\* \* \* \* \*